United States Patent
Lootz et al.

(10) Patent No.: US 9,005,265 B2
(45) Date of Patent: Apr. 14, 2015

(54) STENT HAVING RADIALLY EXPANDABLE MAIN BODY

(75) Inventors: Daniel Lootz, Rostock (DE); Bettina Surber, Duebendorf (CH); Daniel Wintsch, Zurich (CH); Johannes Riedmuller, Nuremberg (DE)

(73) Assignee: BIOTRONIK VI Patent AG, Baar (CH)

( * ) Notice: Subject to any disclaimer, the term of this patent is extended or adjusted under 35 U.S.C. 154(b) by 713 days.

(21) Appl. No.: 12/977,194

(22) Filed: Dec. 23, 2010

(65) Prior Publication Data

US 2011/0093061 A1 Apr. 21, 2011

Related U.S. Application Data

(62) Division of application No. 12/057,806, filed on Mar. 28, 2008, now abandoned.

(30) Foreign Application Priority Data

Mar. 31, 2007 (DE) .......................... 10 2007 015 670

(51) Int. Cl.
*A61F 2/06* (2013.01)
*A61F 2/91* (2013.01)
(Continued)

(52) U.S. Cl.
CPC . *A61F 2/91* (2013.01); *A61F 2/915* (2013.01); *A61F 2/958* (2013.01);
(Continued)

(58) Field of Classification Search
USPC ............. 623/1.21, 1.1, 1.12, 1.16, 1.36, 1.22, 623/1.38, 1.34, 2.11
See application file for complete search history.

(56) References Cited

U.S. PATENT DOCUMENTS 5,741,327 A 4/1998 Frantzen
6,251,135 B1 * 6/2001 Stinson et al. ............... 623/1.34
(Continued)

FOREIGN PATENT DOCUMENTS

DE 19633901 2/1998
DE 19728337 1/1999
(Continued)

OTHER PUBLICATIONS

Search Report for German Patent Application No. 10 2007 015 670.9; Jan. 21, 2008.
(Continued)

*Primary Examiner* — Gregory Anderson
*Assistant Examiner* — Christina Lauer
(74) *Attorney, Agent, or Firm* — Greer, Burns & Crain, Ltd.

(57) ABSTRACT

A stent made of a material having a low strength and having a main body circumscribing a cylindrical shape and radially expandable from a contracted starting position into a dilated support position, comprising a) a plurality of support segments disposed around the circumference and arrayed on one another in the axial direction each segment being formed by a strut meandering in its coarse structure in its contracted starting position and having alternately opposing meandering curves expandable into the support position made of flexible material; b) a plurality of axial connectors connecting between zenith points of at least a part of the meandering curves in the axial-parallel direction of the support segments; (c) a plurality of x-ray marker projections, and d) at least one stabilizer for stabilizing the strut coarse structure in its contracted starting position against radial expansion and being automatically detachable upon radial expansion.

20 Claims, 6 Drawing Sheets (51) Int. Cl.
*A61F 2/915* (2013.01)
*A61F 2/958* (2013.01)
*A61F 2/95* (2013.01)

(52) U.S. Cl.
CPC .............. *A61F 2002/91533* (2013.01); *A61F 2002/91575* (2013.01); *A61F 2002/91591* (2013.01); *A61F 2002/9505* (2013.01); *A61F 2250/0071* (2013.01); *A61F 2250/0098* (2013.01); *A61F 2230/0013* (2013.01)

(56) References Cited

U.S. PATENT DOCUMENTS

| | | | |
|---|---|---|---|
| 6,293,966 | B1 | 9/2001 | Frantzen |
| 2002/0120327 | A1* | 8/2002 | Cox et al. .................. 623/1.16 |
| 2002/0188347 | A1 | 12/2002 | Mathis |
| 2004/0236406 | A1 | 11/2004 | Gregorich |
| 2006/0069424 | A1* | 3/2006 | Acosta et al. ............... 623/1.12 |
| 2007/0073383 | A1 | 3/2007 | Yip et al. |
| 2007/0293938 | A1* | 12/2007 | Gale et al. .................. 623/1.15 |

FOREIGN PATENT DOCUMENTS

| | | |
|---|---|---|
| DE | 10103000 | 8/2002 |
| DE | 102004045224 | 3/2006 |
| DE | 60117563 T | 11/2006 |
| WO | 02055120 A2 | 7/2002 |
| WO | 2004103215 A1 | 12/2004 |
| WO | 2004105642 A1 | 12/2004 |
| WO | 2006029617 A1 | 3/2006 |
| WO | 2006087621 A1 | 8/2006 |
| WO | 2007005800 A1 | 1/2007 |
| WO | 2007117960 A2 | 10/2007 |

OTHER PUBLICATIONS

Search Report for European Patent Application No. 08004044.7; Jul. 24, 2008.

* cited by examiner

STENT HAVING RADIALLY EXPANDABLE MAIN BODY

PRIORITY CLAIM

This patent application is a divisional of co-pending U.S. patent application Ser. No. 12/057,806, filed Mar. 28, 2008, which claims priority to German Patent Application No. 10 2007 015 670.9, filed Mar. 31, 2007, the disclosures of which is incorporated herein by reference in their entirety.

FIELD

The present disclosure relates to expandable vascular stents.

BACKGROUND

One example of a vascular implant is described in detail in International Patent Publication No. WO 2004/103 215 A1, in particular, in regard to the fundamental areas of application of such stents and the special problems upon use of materials having a low ductile yield and also lower strengths, such as magnesium alloys.

In the embodiment which may be inferred from this publication, the stent is implemented by a main body circumscribed by a cylindrical shape and radially expandable from a contracted starting position into a dilated support position which, on one hand, comprises multiple support segments running around the circumference and arrayed in the axial direction on one another. The support segments are each formed by a strut which is meandering in coarse structure in its contracted starting position having alternating opposing meandering curves made of flexible material. On the other hand, the main body has axial connectors running in the axial-parallel direction which connect the support segments between zenith points of at least a part of the meandering curves.

The above-mentioned magnesium alloys as the material for producing stents have significantly lower strength values than typical construction materials for balloon-expandable stents, such as medical steel having the material identifications 316L, MP35N or L 605. These lower strength values cause problems in the practical application of the stents. It is thus necessary for the stent placement to mount the stent on a balloon catheter. For this purpose, the stent, which is structured from a sleeve material by laser cutting, for example, is crimped onto the balloon catheter in its contracted starting position. The stent is also guided on the catheter system through curved areas of the insertion or blood vessel system in this state during the implantation. Individual struts of the stent may open in the corresponding passages, by which the retention forces of the stent on the catheter are reduced. This causes a significant risk of loss of the stent.

Especially endangered areas of the stent are the terminal strut elements having their meandering curves. In addition, the danger arises due to projecting edge segments, the so-called "flaring," that, in addition to the mechanical irritation of the internal vascular wall upon passage of the stenosis or the retraction into the insertion catheter, unintended stripping of the stent from the balloon catheter will occur.

SUMMARY

The present disclosure describes several exemplary embodiments of the present invention.

One aspect of the present disclosure provides a stent made of a material having a low strength and having a main body circumscribing a cylindrical shape and radially expandable from a contracted starting position into a dilated support position, comprising a) a plurality of support segments disposed around the circumference and arrayed on one another in the axial direction, each segment being formed by a strut meandering in its coarse structure in its contracted starting position and having alternately opposing meandering curves expandable into the support position made of flexible material; and b) a plurality of axial connectors connecting between zenith points of at least a part of the meandering curves in the axial-parallel direction of the support segments; and c) at least one means for stabilizing the strut coarse structure in its contracted starting position against radial expansion and being automatically detachable upon a radial expansion of the stent.

One feature of the present disclosure provides a stent of the type according to the species in such a manner that unintended expansion of the entire stent or exposed areas thereof, such as the terminal front edges, is reliably prevented during the implantation.

This feature is achieved according to the present disclosure by a means for stabilizing the strut coarse structure in its contracted starting position against radial expansion which are integrated in the stent design. These stabilization means are then detachable automatically upon the actual radial expansion of the stent.

These stabilization means advantageously secure radial locking of the stent in its crimped state so that unintended expansion of the stent, even in partial areas, is avoided because of this fixing.

According to preferred embodiments of the present disclosure, these stabilization means may be implemented in different ways, for example, by detachable glued joints between adjacent meandering curves of a strut or from strut to strut, by catch elements in the stent structure, boundary fixing traverses or by fine structure struts against the cited "flaring." More detailed explanations may be inferred from the following description, in which exemplary embodiments of the subject matter of the present disclosure are explained in greater detail on the basis of the attached drawings.

BRIEF DESCRIPTION OF THE DRAWINGS

Various aspects of the present disclosure are described hereinbelow with reference to the accompanying figures.

DETAILED DESCRIPTION

Figure 1:
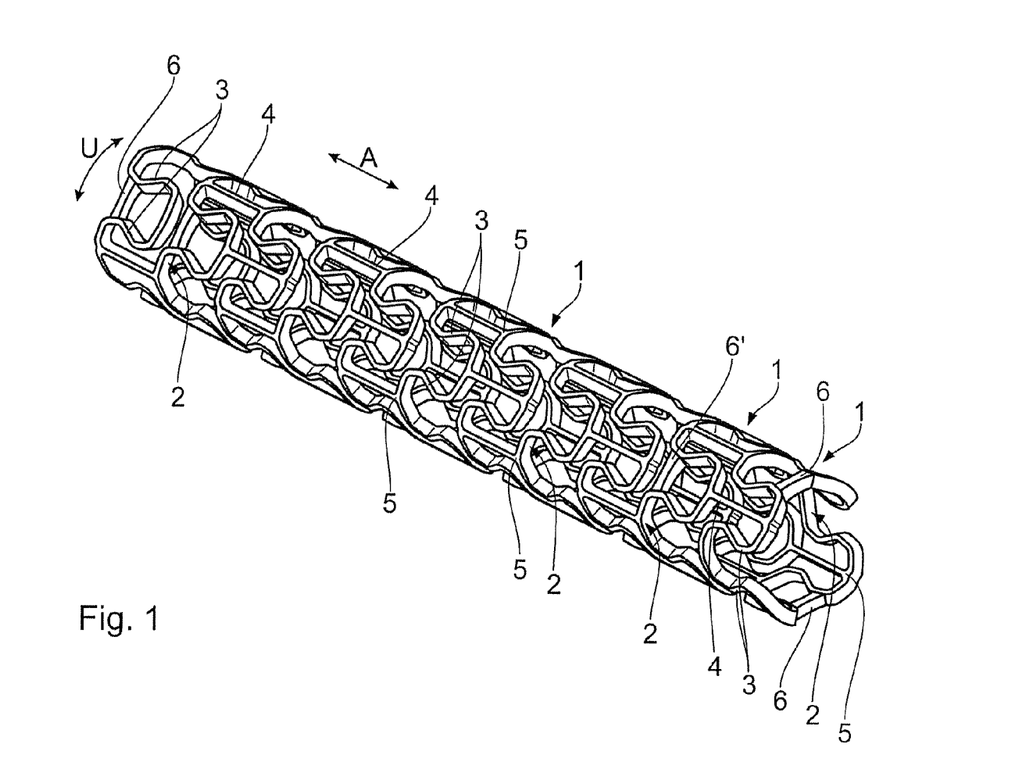
FIG. 1 is a perspective view of one exemplary embodiment of a stent in its contracted starting position having a terminal glued joint as the stabilization means.

FIG. 1 clarifies the structure of the stent in its contracted starting position. The stent is worked out of a cylindrical metal body by laser cutting in such a manner that the stent has multiple support segments 1 running around the circumference U and arrayed in the axial direction A on one another, which are each formed by one of the struts 2 meandering in their coarse structure in the contracted starting position shown.

In the direction parallel to the axial direction A, the support segments 1 are connected to one another by axial connectors 4, which each run between the zenith points 5 of meandering curves 3 to be connected. The axial connectors 4 always run from the exterior side of a meandering curve 3 to the interior side of the meandering curve 3 of the adjacent strut due to the offset of the adjacent support segments 1 around the circumference U.

As is not shown in greater detail in the drawings, upon radial expansion of the stent, the sections of the meandering curves 3 running between the zenith points 5 are deployed around the circumference U. The closer the corresponding sections approach to the circumference U, the greater the so-called collapsing pressure of the stent.

Figure 2:
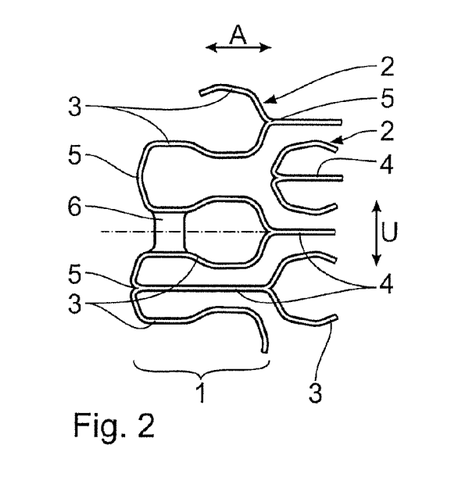
FIG. 2 is a detail top view of the stent in an unwound view having a glued joint variant.
Figure 3:
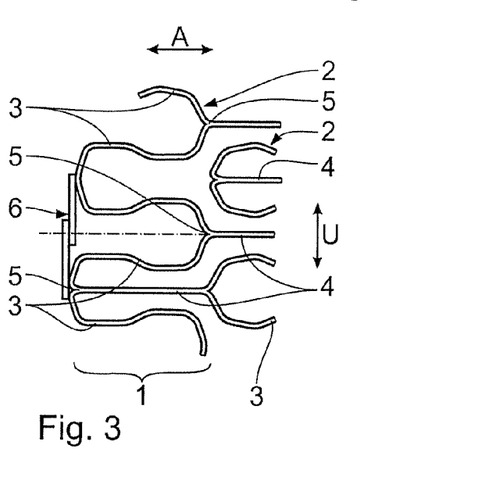
FIG. 3 is a detail top view of the stent in an unwound view having a different glued joint variant.

To achieve the additional radial fixing of the stent desired according to the present disclosure, in the variants shown in FIGS. 1-3, a glued joint 6 is provided which may be applied between the two terminal meandering curves 3 on diametrically opposite radial positions in the form of a grouting point, for example. This glued joint 6 is shown schematically in FIG. 2. With this type of glued joint 6, the adhesive faces are loaded by tension.

In another exemplary embodiment, it is also possible to attach the glued joint 6 in such a manner that the adhesive faces are loaded by shear, as indicated in FIG. 3.

The individual points of the glued joint 6 may not only be situated terminally, as shown in FIGS. 1-3, but also distributed on the circumference over the length of the stent 1. With such multiple positioning, upon radial expansion of the stent, the fixing is detached automatically in chronological sequence in accordance with the retention force. Experiments have shown that in spite of asymmetrical detachment of the individual fixed points, the stent may be open homogeneously if the fixing force is only large enough that the axial connectors 4 are still capable of absorbing it. If glued joints 6' are positioned in the area of the particular strut 2 second from the outside, for example, the axial connectors 4 may also act on the glued joint 6' from both sides which favors homogeneous opening behavior. In this case, the outermost strut 2 is either to be as short as possible or have the fine structures described in greater detail on the basis of FIGS. 7 and 8 on the edge to suppress flaring.

Figure 4:
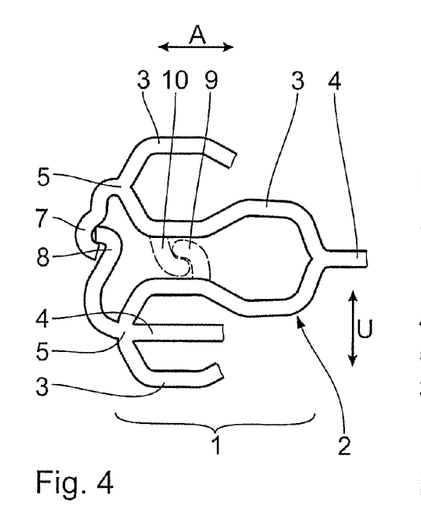
FIG. 4 is a schematic detail excerpt in an unwound illustration of the stent having catches as the stabilization means.

FIG. 4 shows a further exemplary embodiment for the stabilization means for additional radial fixing of the stent. Two neighboring meandering curves 3 of a strut 2 are coupled to one another in the contracted starting position at their edges by hooked catch elements 7, 8. When the stent is transferred into its contracted starting position, the so-called crimping, the catch elements 7, 8 are engaged with one another. The stent is thus held together at its edge, so that the "flaring" cited hereinabove is avoided. During the radial expansion, the engagement between elements 7, 8 is broken open and the stent may open homogeneously.

In a further exemplary embodiment, the configuration of catch elements in the form of hooked projections 9, 10 in the interior of a meandering curve 3 is shown by dashed lines in FIG. 4. This fixing is also produced during crimping by hooking of the projections 9, 10 and broken upon expansion of the stent. It is recognizable that the hooked projections 9, 10 may be provided on arbitrary struts 2 along the stent.

Figure 5:
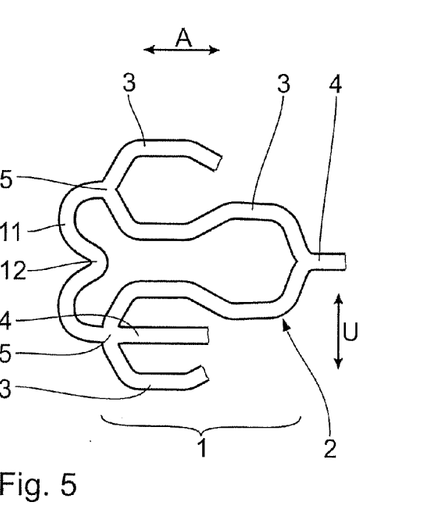
FIG. 5 is a schematic detail excerpt in an unwound view of a stent having a boundary fixing traverse.
Figure 6:
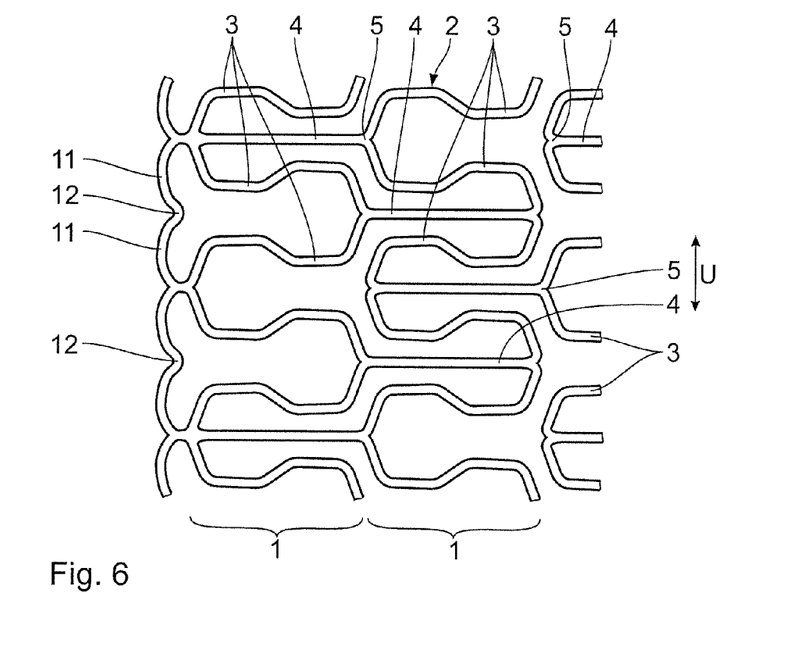
FIG. 6 is a schematic detail excerpt in an unwound view of an exemplary embodiment of a stent having a different boundary fixing traverse.

FIGS. 5 and 6 show further exemplary embodiments of the stabilization means for the additional radial fixing of the stent in the cramped state. In these embodiments, fixing traverses 11 shaped in one piece on the boundary struts 2 are provided which connect to the adjacent meandering curves 3 of a strut 2 from zenith point 5 to zenith point 5. While only one fixing traverse 11 is provided in FIG. 5, in the exemplary embodiment shown in FIG. 6, the boundary of the stent is completely terminated by a row of fixing traverses 11.

Each fixing traverse 11 has a double-arched course having a central bend 12 which acts as the intended breakpoint upon radial expansion of the stent. The stent, as already described in connection with the glued joint 6, may expand homogeneously by the tearing of the fixing traverses 11.

Figure 7:
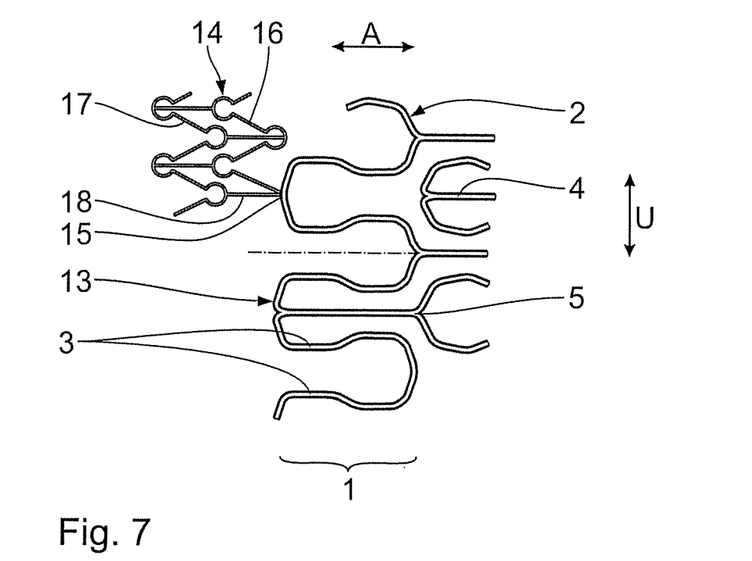
FIG. 7 is a schematic detail view in an unwound view of an exemplary embodiment of a stent having boundary fine structure struts as the stabilization means.
Figure 8:
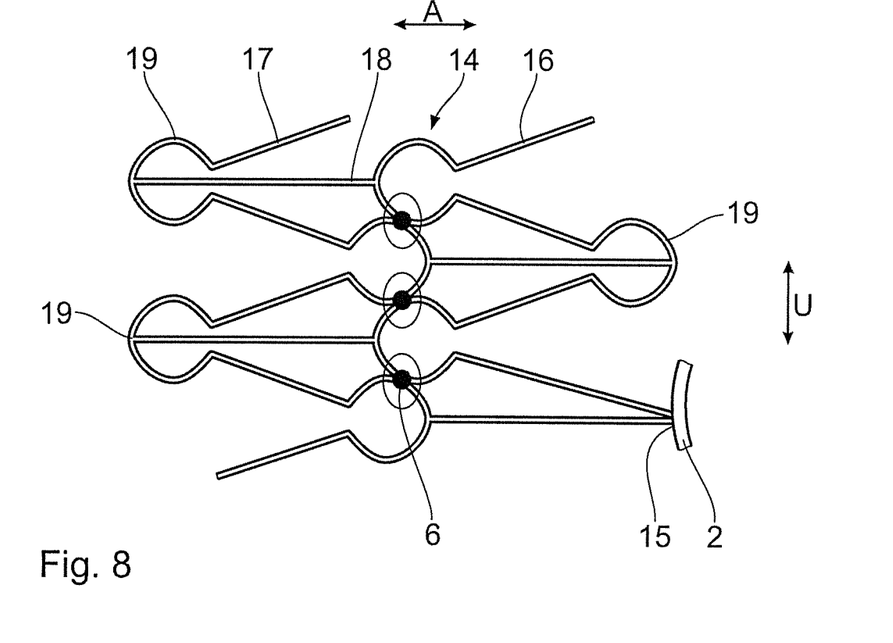
FIG. 8 is an enlarged detail excerpt as shown in FIG. 7.

A further exemplary embodiment of the stabilization means provided according to the present disclosure is shown in FIGS. 7 and 8. These are peripheral fine structure struts 14 on the boundary at the ends 13 of the stent, which are bound to the exterior sides 15 of the meandering curves 3. These fine structure struts 14 are formed in each case by two struts 16, 17 running essentially parallel having coupling struts 18 running in the axial direction. The basic configuration of the fine structure struts 14 is thus ladder-like, the double struts 16, 17 being folded in a zigzag in the lateral plane of the stent. Curved groin points 19 are shaped into the double struts 16, 17 in the bend points, via which the coupling struts 18 may be fastened in one piece while protecting the material in regard to the radial expansion of the fine structure struts 14 at the struts 16, 17. The expandability of the fine structure struts 14 is improved by the curved shape in these groin points 19.

As schematically indicated in FIG. 8, the fine structure struts 14 in the area of the interior groin points 19, which are adjacent to one another in the contracted starting position, are additionally fixed by a glued joint 6 or also catch means (not shown here), for example. The entire stent is thus stabilized on its front-side boundary in the crimped configuration in such a manner that flaring is kept as small as possible. Due to the fixing at the interior groin points 19, the opening forces act on both sides of this fixing, so that higher fixing forces may be overcome without impermissibly distorting the stent structure.

Figure 9:
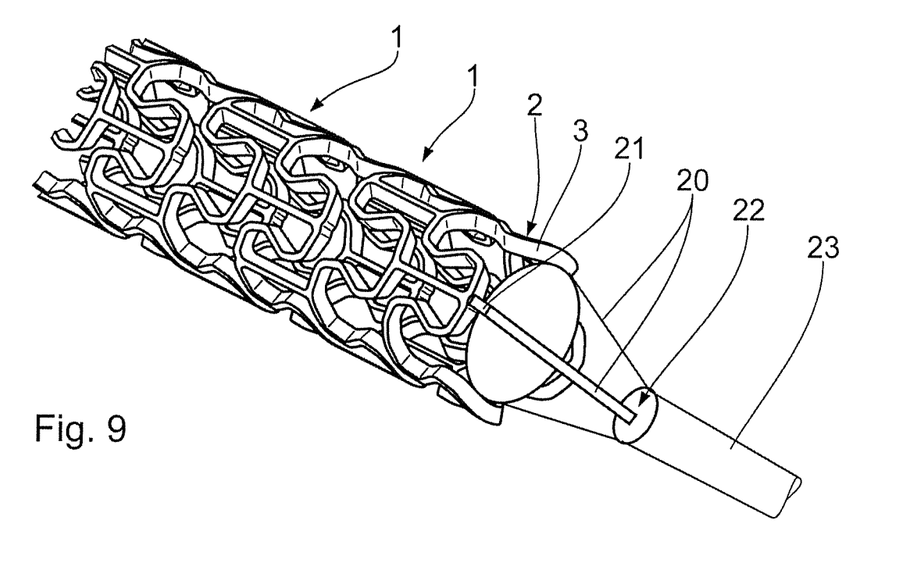
FIG. 9 is a perspective partial illustration of an exemplary embodiment of a stent having extension struts for removable fastening to a balloon catheter.
Figure 10:
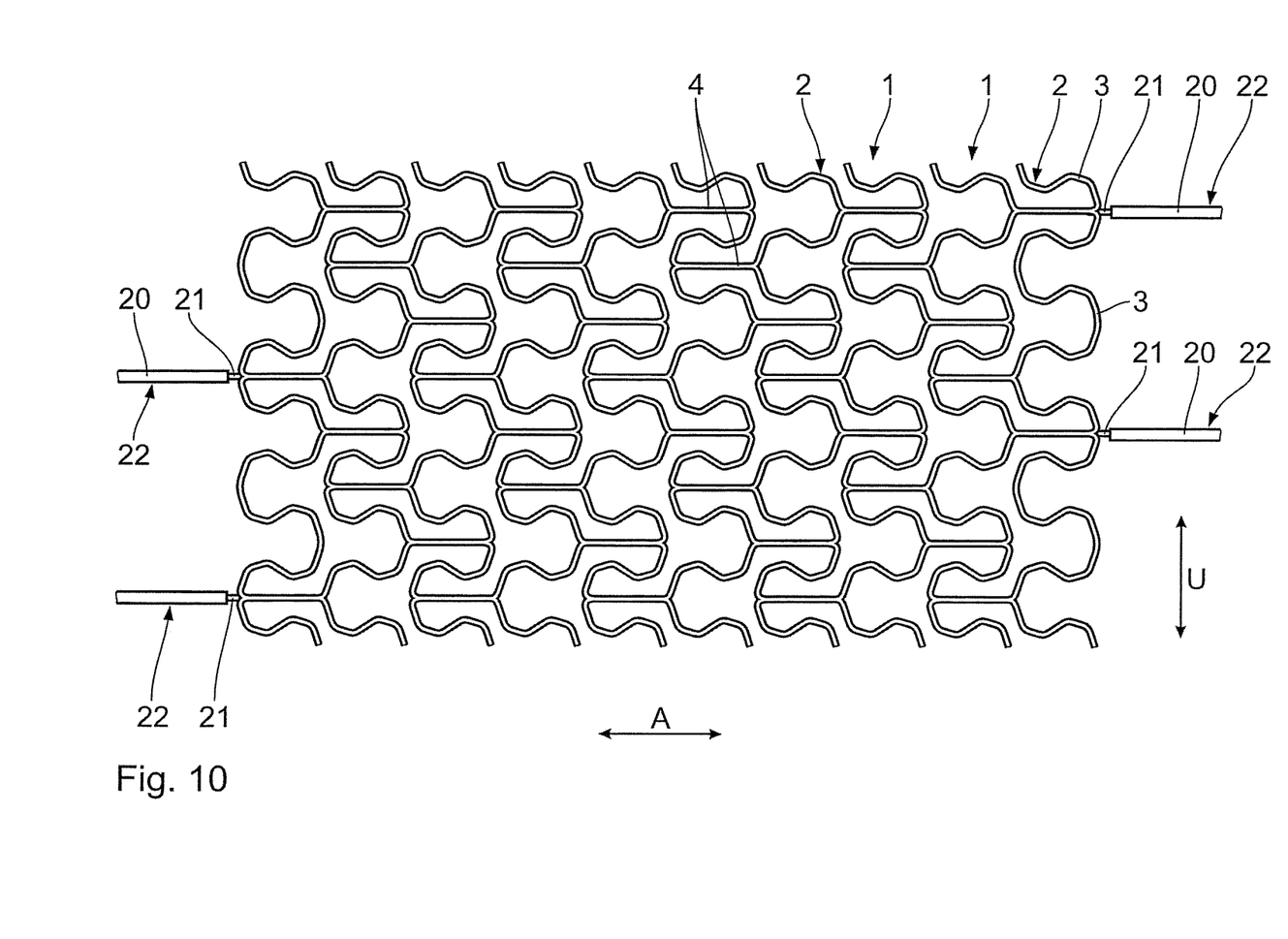
FIG. 10 is a top view of the stent as shown in FIG. 9 in an unwound view.

A further exemplary embodiment of the stabilization means for additional radial fixing of the stent is illustrated in FIGS. 9 and 10. These are extension struts 20, which run essentially in the axial direction A and are bound to the strut at one end via an intended breakpoint 21 to the external strut 2. The free end 22 of the extension struts 20 is permanently fastened in each case in a suitable manner to a balloon catheter 23, only schematically indicated in FIG. 9.

The extension struts 21 again counteract a radial expansion of the meandering curves 3 of the external struts 2, in particular, which suppresses flaring. Upon dilation of the stent, the intended breakpoints 21 are torn and the stent is thus released from the extension struts 20.

Figure 11:
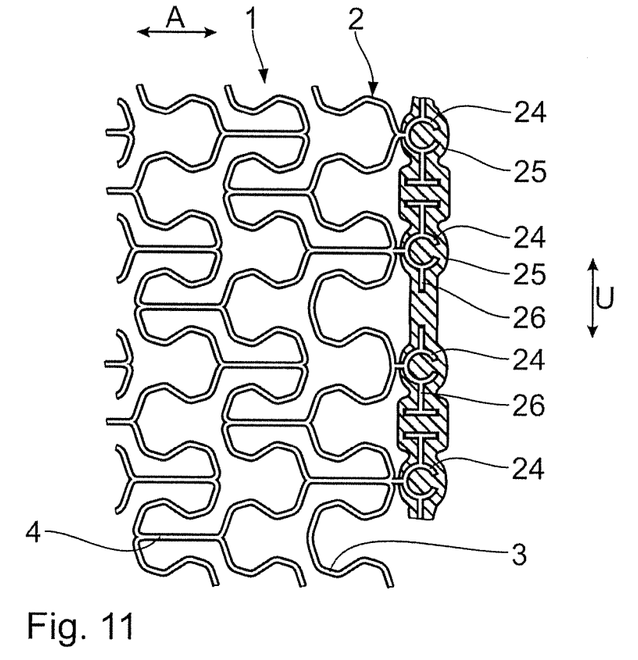
FIG. 11 is a detail top view of an exemplary embodiment of a stent in an unwound view having marker projections coupled to one another.
Figure 12:
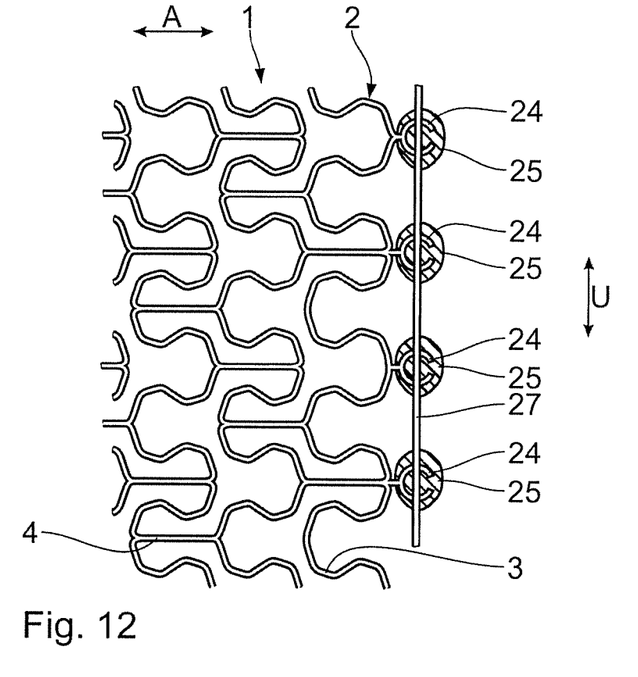
FIG. 12 is a detail top view of an exemplary embodiment of a stent in an online view having marker projections coupled in a ring.

Exemplary embodiments for stabilization means against flaring shown in FIGS. 11 and 12 use the x-ray marker projections 24 often present in stents, which are formed as eye-shaped projections onto the meandering curves 3 of the external struts 2 and are provided with a thermoplastically moldable marker polymer coating 25. To use these elements, which are known in stents, as stabilization means against flaring, the x-ray marker projections 24 having their marker polymer coating 25 are designed in such a manner that the x-ray marker projections 24 contact one another after the crimping of the stent and are reshaped into a peripheral ring by a thermal treatment of the marker polymer coating 25. The ring formation is supported by transverse connection elements 26 protruding in the peripheral direction from the x-ray marker projections 24, which may be designed as either I-shaped or T-shaped in a top view.

Finally, it is still possible, as shown in FIG. 12, to equip stents with polymer-coated x-ray marking projections 24 against flaring in such a manner that a peripheral ring made of magnesium, for example, is pushed onto the projections 24 having their coating 25 which is embedded therein by heating and brief melting of the marker polymer coating 25 and thus fixed. The ring 27 may comprise rigid material or wire, and may also be laid on only a partial circumferential length around the stent.

All patents, patent applications and publications referred to herein are incorporated by reference in their entirety.

What is claimed is:

1. A stent, having a main body circumscribing a cylindrical shape having an axis and radially expandable from a contracted starting position into a dilated support position, comprising:
    (a) a plurality of flexible support segments, spaced around the circumference of the main body and arrayed in an axial direction, each support segment being formed by a strut meandering in its coarse structure in its contracted starting position, and having alternately opposing meandering curve sections expandable into the dilated support state;
    (b) a plurality of axial connectors each connecting between a zenith point of one meandering curve section and a second meandering curve section in the axial-parallel direction of the support segments; and
    (c) a plurality of stabilizer elements for stabilizing the main body in a contracted starting state against undesired radial expansion the plurality of stabilizer elements comprising:
    a plurality of x-ray marker projections connected to the struts and projecting from a terminal one of the flexible support segments of the main body and spaced around the circumference of the main body, the x-ray marker projections being coated with marker polymer, the marker polymer forming a ring projecting from the terminal one of the flexible support segments of the main body connecting the x-ray marker projections in the contracted state and automatically detachable upon radial expansion of the stent into the dilated support position.

2. The stent of claim 1, wherein the x-ray marker projections comprise a plurality of radially oriented transverse connection elements attached to a base.

3. The stent of claim 2, wherein the radially oriented transverse connection elements are T-shaped or I-shaped.

4. The stent of claim 1, wherein the x-ray marker projections are in non-interlocking contact in the contracted state.

5. The stent of claim 1, wherein the x-ray marker projections are C-shaped.

6. A stent, having a main body circumscribing a cylindrical shape having an axis and radially expandable from a contracted starting position into a dilated support position, comprising:
    (a) a plurality of flexible support segments, spaced around the circumference of the main body and arrayed in an axial direction, each support segment being formed by a strut meandering in its coarse structure in its contracted starting position, and having alternately opposing meandering curve sections expandable into the dilated support state;
    (b) a plurality of axial connectors each connecting between a zenith point of one meandering curve section and a second meandering curve section in the axial-parallel direction of the support segments; and
    (c) a plurality of stabilizer elements for stabilizing the main body in a contracted starting state against undesired radial expansion the plurality of stabilizer elements comprising:
    a plurality of x-ray marker projections connected to the struts and projecting from a terminal one of the flexible support segments of the main body and spaced around the circumference of the main body, the x-ray marker projections being coated with marker polymer, the marker polymer forming a ring connecting the x-ray marker projections in the contracted state, the x-ray marker projections being in non-interlocking contact in the contracted state, and automatically detachable upon radial expansion of the stent into the dilated support position.

7. The stent of claim 6, wherein the x-ray marker projections comprise a plurality of radially oriented transverse connection elements attached to a base.

8. The stent of claim 7, wherein the radially oriented transverse connection elements are T-shaped or I-shaped.

9. The stent of claim 6, wherein the x-ray marker projections are C-shaped.

10. A stent, having a main body circumscribing a cylindrical shape having an axis and radially expandable from a contracted starting position into a dilated support position, comprising:
    (a) a plurality of flexible support segments, spaced around the circumference of the main body and arrayed in an axial direction, each support segment being formed by a strut meandering in its coarse structure in its contracted starting position, and having alternately opposing meandering curve sections expandable into the dilated support state;
    (b) a plurality of axial connectors each connecting between a zenith point of one meandering curve section and a second meandering curve section in the axial-parallel direction of the support segments; and
    (c) a plurality of stabilizer elements for stabilizing the main body in a contracted starting state against undesired radial expansion the plurality of stabilizer elements comprising:
    a plurality of x-ray marker projections connected to the struts at an end of the main body and spaced around the circumference of the main body, the x-ray marker projections being coated with marker polymer, a peripheral ring attached to the x-ray marker projections in the contracted state.

11. The stent of claim 10, wherein the peripheral ring covers a portion of the circumference of the main body.

12. The stent of claim 10, wherein the peripheral ring covers the entire the circumference of the main body.

13. The stent of claim 10, wherein the peripheral ring is attached to the x-ray marker projections using the marker polymer.

14. The stent of claim 10, wherein the peripheral ring is embedded in the marker polymer.

15. The stent of claim 10, wherein the peripheral ring comprises a rigid material.

16. The stent of claim 10, wherein the peripheral ring comprises magnesium.

17. The stent of claim 10, wherein the x-ray marker projections comprise a plurality of radially oriented transverse connection elements connected to a base.

18. The stent of claim 17, wherein the radially oriented transverse connection elements are either T-shaped or I-shaped.

19. The stent of claim 10, wherein the x-ray marker projections are in non-interlocking contact in the contracted state.

20. The stent of claim 10, wherein the x-ray marker projections are C-shaped.

* * * * *